United States Patent
Zolten

(12) 
(10) Patent No.: US 6,352,345 B1
(45) Date of Patent: *Mar. 5, 2002

(54) METHOD OF TRAINING AND REHABILITATING BRAIN FUNCTION USING HEMI-LENSES

(75) Inventor: A. J. Zolten, Little Rock, AR (US)

(73) Assignee: Comprehensive Neuropsychological Services LLC, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/706,920

(22) Filed: Nov. 6, 2000

Related U.S. Application Data

(63) Continuation of application No. PCT/US98/27508, filed on Dec. 17, 1998.

(51) Int. Cl.$^7$ ................................................ A61B 3/00
(52) U.S. Cl. ...................................................... 351/219
(58) Field of Search ................................ 351/246, 247, 351/160 R, 162, 177, 203, 45, 46, 205, 219, 44, 47, 48, 49, 161, 163

(56) References Cited

U.S. PATENT DOCUMENTS

| | | |
|---|---|---|
| 1,802,424 A | 4/1931 | Hitchiner |
| 2,139,213 A | 12/1938 | Verre |
| 4,324,461 A | 4/1982 | Salvatori |
| 4,744,647 A | 5/1988 | Meshel et al. |
| 5,008,102 A | 4/1991 | York |
| 5,139,323 A | 8/1992 | Schillo |
| 5,182,588 A | 1/1993 | Maurer et al. |
| 5,305,027 A | 4/1994 | Patterson |
| 5,424,786 A | 6/1995 | McCarthy |
| 5,434,630 A | 7/1995 | Bransome |
| 5,440,359 A | 8/1995 | Bloch-Malem |
| 5,483,304 A | 1/1996 | Porat |
| 5,489,953 A | 2/1996 | Griffith |
| 5,502,518 A | 3/1996 | Lieberman |
| 5,570,142 A | 10/1996 | Lieberman |
| 5,570,144 A | 10/1996 | Lofgren-Nisser |
| 5,662,706 A | 9/1997 | Legerton et al. |
| 5,886,769 A | 3/1999 | Zolten |
| 6,062,687 A | * 5/2000 | Lofgren-Nisser ............ 351/46 |

FOREIGN PATENT DOCUMENTS

| | | |
|---|---|---|
| WO | WO 99/59461 | 11/1999 |

OTHER PUBLICATIONS

Fouty, H., et al., "A Novel Contact–Lens System to Assess Visual Hemispheric Asymmetries," *Perceptual and Motor Skills*, 1992, pp. 567–575.

Harrell, E., et al., "Performance of Subjects with Left Visual Neglect after Removal of the Right Visual Field Using Hemifield Goggles," *Journal of Rehabilitation*, Oct./Nov./Dec. 1995, pp. 46–49.

* cited by examiner

Primary Examiner—George Manuel
(74) Attorney, Agent, or Firm—Ray F. Cox, Jr.

(57) ABSTRACT

A method of rehabilitation or training of targeted portions of the brain in which hemi-lenses having semi-opaque radial segments selectively blind portions of the visual processing areas of the brain to force visual processing to a particular portion of the brain which is thereby stimulated. Such rehabilitation consists of having the patient perform visual and non-visual tasks constructed to activate processing in the targeted portion of the brain. The hemi-lenses may be employed in a series of gradually increased translucency to allow the patient's visual system to adapt in stages to the rehabilitated balance between intact visual processing and relearned visual processing.

18 Claims, 4 Drawing Sheets

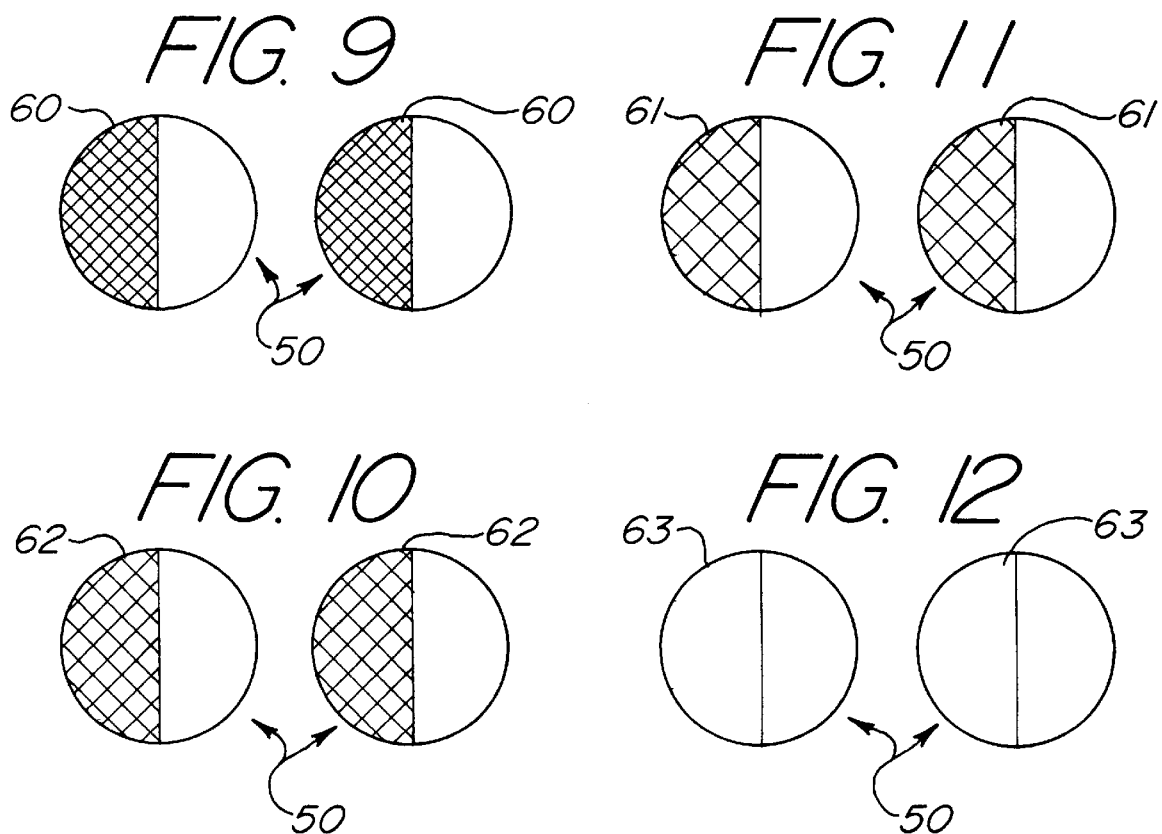

METHOD OF TRAINING AND REHABILITATING BRAIN FUNCTION USING HEMI-LENSES

This application is a Continuation of PCT/US98/27508 filed Dec. 17, 1998.

BACKGROUND OF THE INVENTION

The present invention relates to training and rehabilitating brain function, and in particular, to the use of hemi-lens to accomplish this purpose.

Brain injury, such as Cerebral Vascular Accident (stroke), closed head injury, penetrating head wounds, and invasive growths can generate a variety of sensory/perceptual and other cognitive disturbances that significantly impact the ability of individuals to maintain independence in their environments. When this insult occurs in the posterior regions of the brain, especially the parietal and/or occipital lobes, a change in the functioning of the visual perceptual system can occur. These sensory/perceptual disturbances involve inattention to visual stimuli to a varying degree, from mild inattention to details to complete loss of recognition of visual information in a given visual field. In some instances, perception of the visual field disappears completely.

Rehabilitation of the patient with a visual perceptual defect is limited. Most techniques involve behavioral and/or cognitive training directed at focused extra attention to the visual field that has been disrupted. The results of this type of rehabilitation have been successful, but limited.

Recent evidence showing that attention plays an essential role in almost all other brain functions including motor functioning in stroke patients with hemiparesis or hemiplegia, suggests that any technique that can improve attention related to brain injury might help in the recovery of many non-vision related brain functions. In addition, some research has established a relationship between hemispheric attention and visual processing in the dysfunction of developmental reading disorder, the most common type of learning disability.

Furthermore such improvement in brain function could also be effective in visual training in non-medical settings. For example, baseball batters use asymmetric visual information when standing at the plate judging pitches. Isolating the field that captures the pitcher and pitch, and blocks the catcher, umpire, and other distractions might significantly improve batting performance.

Contact lens, glasses and the like are known in which areas of the lens are rendered opaque or semi-opaque for the purpose of correcting defects in vision or to shield the eye from damage.

Harrell, E. H., T. Kramer-Stutts, and A. J. Zolten, "Performance of Subjects with Left Visual Neglect after Removal of the Right Visual Field Using Hemifield Goggles," *Journal of Rehabilitation*, (October/November/December 1995), pp.1 46–49, discloses improved performance with visual input directed to a neglected field when the non-neglected field is occluded. Harrell et al. disclose complete occlusion of the visual field directed to one hemisphere of the brain.

Harrell et al. disclose changing the amount of visual field input by adjusting the Velcro strips which provide the occlusion over the goggles used in the experiment described in the article. Harrell et al. do not, however, disclose the use of a series of lenses of varying degrees of opacity, such as semi-opaque areas, in the course of visual retraining.

While Harrell et al. suggest that in the future a procedure using contact lenses might be preferable to goggles, they conclude that this would be expensive and probably not feasible for practical applications in rehabilitation.

One of the problems in using contact lens having occluded areas is that the contact lens must sit on the eye without rotation. Various techniques are known for maintaining the position of a contact lens without rotation. For example, such techniques are disclosed in U.S. Pat. Nos. 4,324,461; 5,483,304; 5,502,518; and 5,570,142. Also, various techniques are known for manufacturing contact lenses with opaque areas.

SUMMARY OF THE INVENTION

The present invention is method of using a hemi-lens contact lens product to selectively block visual sensory input to a specific portion of the brain. The term "hemi-lens" is used herein to refer to a lens having portions of the lens occluded by opaque or semi-opaque material.

The "blinding" of the sensory-blocked portion of the brain forces processing of all primary visual information to the remaining portions of the brain. This technique is useful in the rehabilitation of visual field defects, training of brain function and for other purposes.

For example, if the left halves of each of a pair of contact lenses are rendered opaque (e.g., by patching the left half of each lens with black non-translucent contact lens plastic) visual processing is forced to the right hemisphere of the brain thereby stimulating that area of the brain. Occluding the right halves of each of a pair of contact lenses with opaque material would stimulate the opposite hemisphere.

Specific areas of the brain are targeted by selectively blinding portions of each of a pair of contact lenses over more or less than a full hemisphere. For example, a particular quarter segment of each lens could be rendered clear or the remaining ¾ segment could be rendered opaque. Various combinations of blocked portions of the contact lenses may therefore be utilized to force visual processing to a particular portion of the brain that is thereby stimulated. Each contact lens is weighted or otherwise constructed so that the lenses sit on the eye without rotating.

The method of using the hemi-lens to rehabilitate a patient with a visual defect or training specific visual processing areas consists of having the patient perform visual and non-visual tasks constructed to activate processing in the targeted portion of the brain. A graduated series of hemi-lenses are constructed of semi-transparent material of varying degrees of opacity to allow the patient's visual system to adapt in stages to the rehabilitated balance between intact visual processing and relearned visual processing.

It is therefore an object of the present invention to provide for a method of using a contact lens product having occluded segments to force visual processing to targeted areas of the brain to encourage rehabilitation and training of such targeted areas.

It is a further object of the present invention to provide for such a method employing a series of contacts lens having graduated degrees of opacity to allow the patient's vision to adapt in stages to rehabilitation and training.

These and other objects and advantages of the present invention will be apparent from a consideration of the following detailed description of the preferred embodiments in conjunction with the appended drawings as described following.

BRIEF DESCRIPTION OF THE DRAWINGS

FIGS. 9, 10, 11, and 12 are elevational views of pairs of contact lens with occluded areas having varying degrees of opacity ranging from most opaque (FIG. 9) to least opaque (FIG. 12).

DETAILED DESCRIPTION OF THE PREFERRED EMBODIMENTS

The present invention uses a contact lens product ("hemi-lens") to selectively block visual sensory input to a specific targeted portion of the brain. This "blinding" of the sensory blocked portion of the brain forces processing of all primary visual information to the remaining unblocked portion. This forced processing paradigm can be used in the rehabilitation of visual field defects including visual hemineglect and/or hemi-inattention, as well as homonymous hemianopsia. Hemi-lenses can also be used in the rehabilitation of other attention problems related to brain injury including spatial attention, motor control, memory problems, language disturbances and other brain-injury problems associated with asymmetric brain insult.

Figure 1:
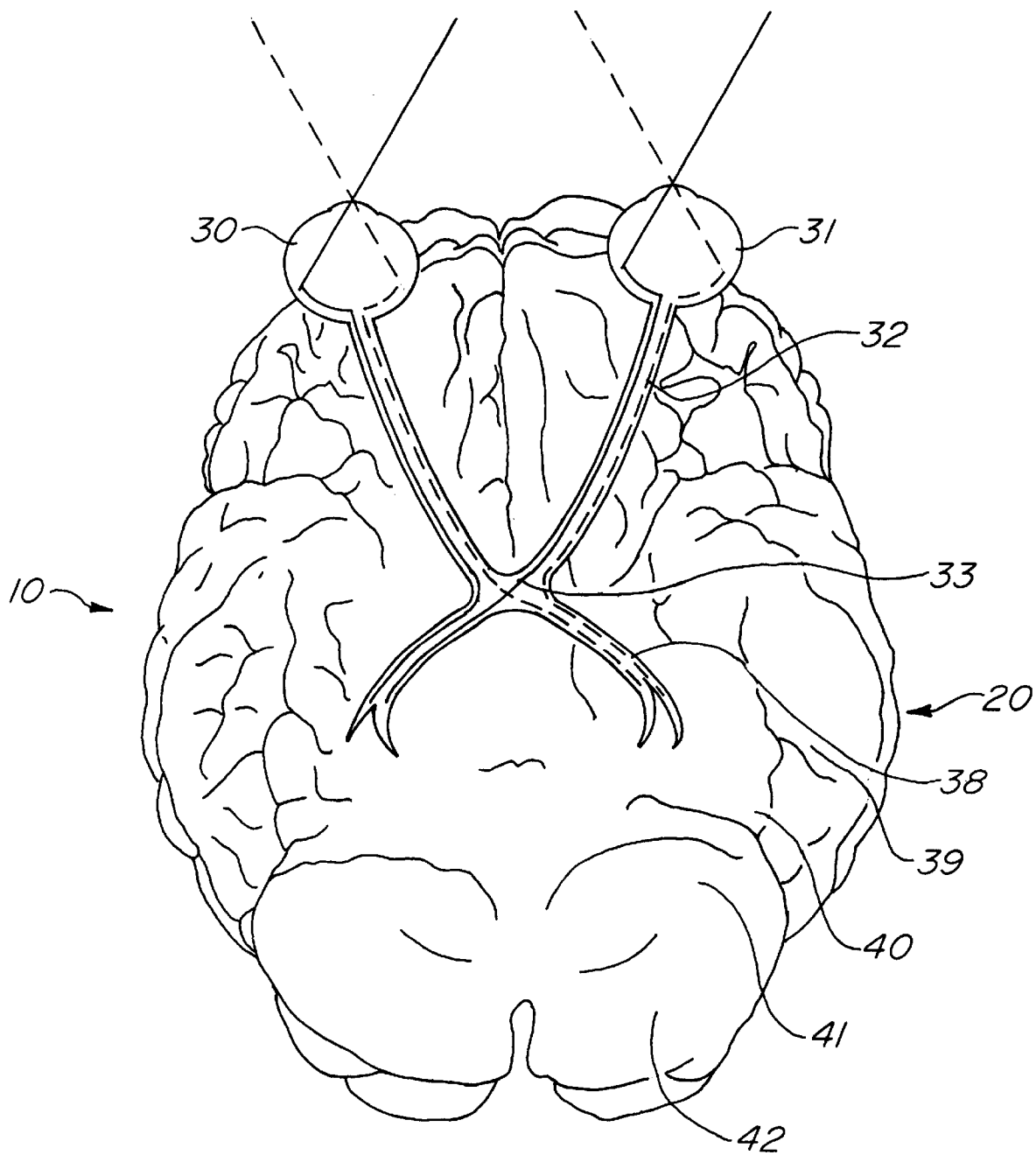
FIG. 1 is a horizontal (coronal) cross section of a human brain through the central axis of the eyes illustrating various portions of the brain involved in visual processing.
Figure 2:
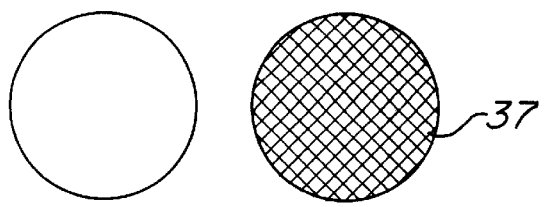
FIG. 2 is a schematic diagram of the effect on the left and right visual field as a result of injury to an optic nerve.

The action of the present invention may be described with reference to FIG. 1. Visual perception is redundantly provided to both hemispheres 10, 20 of the brain independently by each eye 30, 31. This allows for binocular vision and depth perception. The lateral visual field of each eye projects visual information to the ipsilateral visual cortex and the medial visual field of each eye projects visual information across to the contralateral visual cortex.

The focused retraining of the injured portion of the brain is accomplished with the delivery of a vision blocking system that effectively removes incoming visual information to the intact hemisphere of the brain.

Hemi-lenses 50 are designed to eliminate visual information by "patching" a radial segment of each lens with black, non-translucent contact lens plastic. The term "radial segment" is intended herein to refer to a segment of a lens defined by lines radiating outward from the center of the lens. Each contact lens is weighted or otherwise constructed to ensure that the lens sits without rotating on the eye, and remains with the dividing line between blacked out side and visually clear side in a vertical position. Means of accomplishing non-rotation of a contact lens are known in the art.

Figure 3A:
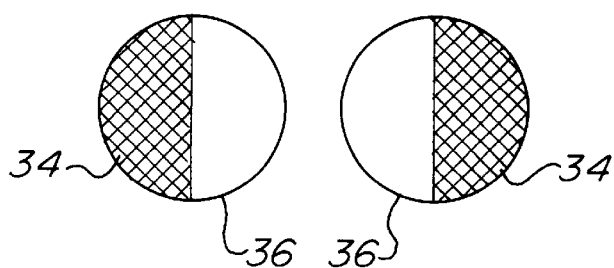
FIG. 3A is a schematic diagram of the effect on the left and right visual field as a result of injury to the optic chiasm.
Figure 3B:
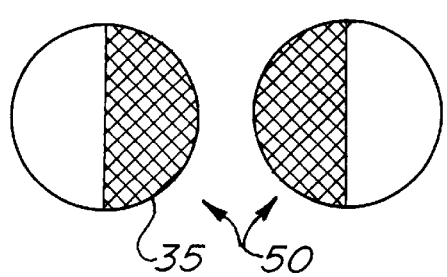
FIG. 3B is an elevational view of a pair of contact lens with occluded areas for forcing visual processing to the injured area schematically illustrated in FIG. 3A.

Focused retraining or rehabilitation may be described with reference to FIGS. 1–8. Injury to an optic nerve 32 produces an effect on the visual field 37 of the injured optical nerve as illustrated schematically in FIG. 2. Complete loss of the visual field of either the left or right eye is not amenable to treatment by the method of the present invention. However, injury to the optic chiasm 33, which results in loss to the lateral visual field 34 as shown in FIG. 3A, may be treated by the use of hemi-lenses having occluded radial segments 35 over the medial visual fields as shown in FIG. 3B, thereby forcing visual processing to the lateral visual fields 36.

Figure 4A:
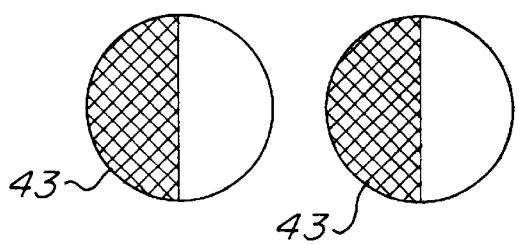
FIG. 4A is a schematic diagram of the effect on the left and right visual field as a result of injury to the optic tract.
Figure 4B:
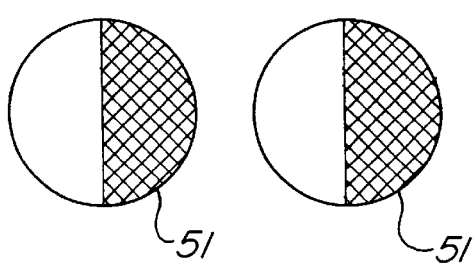
FIG. 4B is an elevational view of a pair of contact lens with occluded areas for forcing visual processing to the injured area schematically illustrated in FIG. 3A.
Figure 5A:
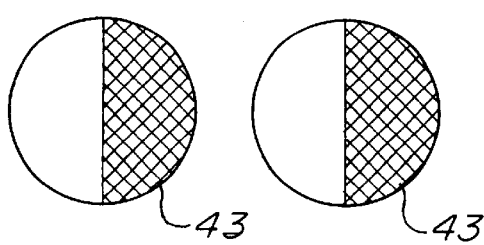
FIG. 5A is a schematic diagram of the effect on the left and right visual field as a result of injury to the anterior parietal lobe.
Figure 5B:
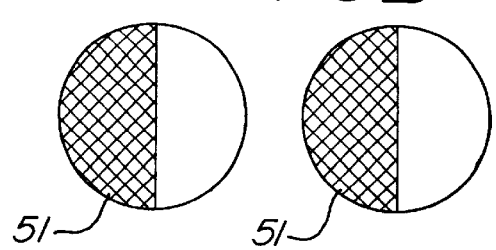
FIG. 5B is an elevational view of a pair of contact lens with occluded areas for forcing visual processing to the injured area schematically illustrated in FIG. 3A.

Injury to the optic tract 38 as shown in FIG. 4A or injury to the anterior parietal lobe 39 as shown in FIG. 5A, results in the loss of either the left or right visual field 43 depending on which hemisphere specific optic tract is injured. The effect of this type of injury on the visual fields is illustrated in FIGS. 4A and 5A. Such injuries may be rehabilitated by the method of the present invention using hemi-lenses 50 having either left or right occluded radial segments 51 to force visual processing to the injured visual field 43.

Figure 6A:
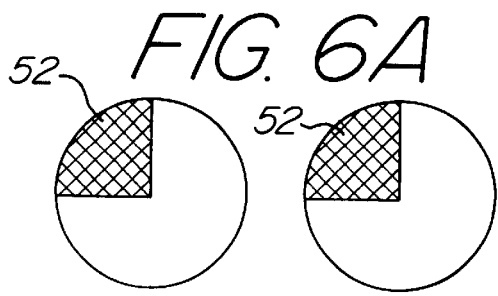
FIG. 6A is a schematic diagram of the effect on the left and right visual field as a result of injury to a portion of the posterior parietal lobe.
Figure 6B:
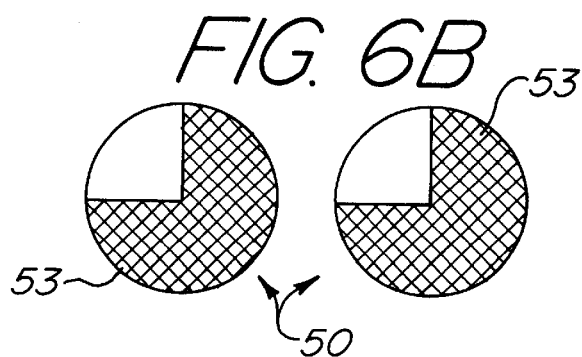
FIG. 6B is an elevational view of a pair of contact lens with occluded areas for forcing visual processing to the injured area schematically illustrated in FIG. 3A.
Figure 7A:
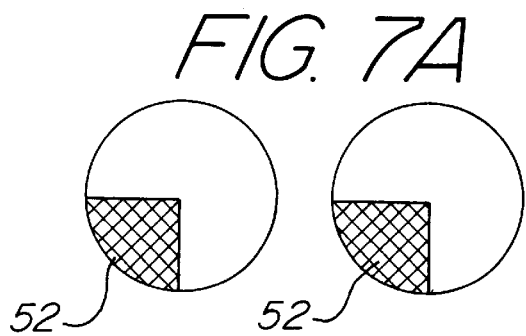
FIG. 7A is a schematic diagram of the effect on the left and right visual field as a result of injury to a portion of the posterior parietal lobe posterior to the injury site of FIGS. 6A and 6B.
Figure 7B:
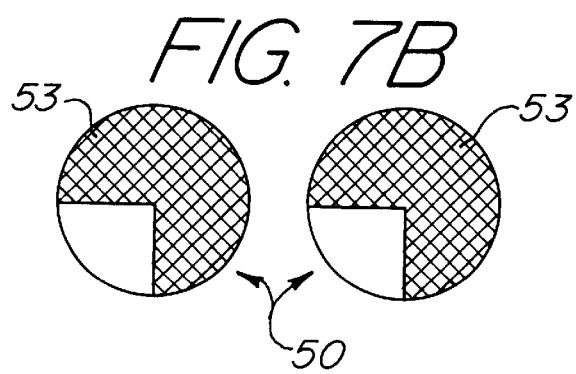
FIG. 7B is an elevational view of a pair of contact lens with occluded areas for forcing visual processing to the injured area schematically illustrated in FIG. 3A.

Injury to portions of the posterior parietal lobe 40, 41 may produce the lose of radial segments of the visual field 52 of less than a full hemisphere as illustrated in FIGS. 6A and 7A. Corresponding hemi-lenses 50 occluding radial segments 53 as illustrated in FIGS. 6B and 7B respectively, force visual processing to the damaged visual fields 52.

Figure 8:
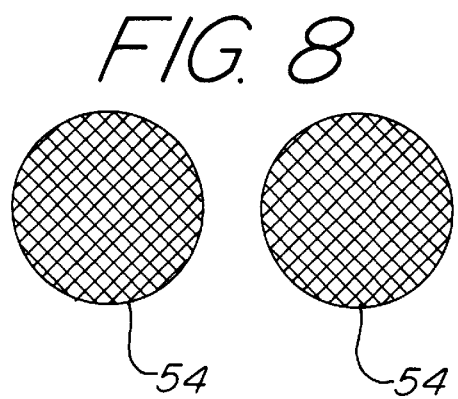
FIG. 8 is a schematic diagram of the effect on the left and right visual field as a result of injury to the occipital lobe.

Injury to the occipital lobe 42 producing the complete loss of the visual field 54 of both eyes as illustrated in FIG. 8 is not amenable to the practice of the present invention.

Rehabilitation of the patient with hemi-lenses consists of visual and non-visual tasks constructed to activate processing in the injured portion of the brain. Visual sensory stimulation obviously occurs, but multimodal sensory stimulation, processing of hemisphere specific tasks, and hemisphere specific motor tasks is also involved in an effort to stimulate the injured areas of the brain with as little interference from the intact brain via sensory blocking.

Alternatively to completely opaque radial segments 60 of each lens, the degree of opacity may vary, from approximately 90% input blockage radial segments 61 to approximately 10% blockage radial segments 62 as illustrated schematically by FIGS. 9–12 in stages of gradually decreasing opacity. By allowing some hemisphere specific visual information to reach the intact visual cortex, contralateral visual sensory matching can occur, with the intact visual field providing some sensory/perceptual architecture to the damaged visual sensory field. Hence, use of semi-opaque hemi-lenses would allow both an increased sensory emphasis on processing visual information with the damaged visual sensory apparatus and allow for that damaged sensory apparatus to derive internal feedback from the intact visual sensory apparatus, located in the spared visual field.

Hemi-lenses constructed of a graduated series of such semi-transparent materials would gradually allow the patient's visual system to adapt to the rehabilitated balance between intact visual processing and relearned visual processing. It is possible that some individuals will demonstrate improved attention and safety with some level of visual blocking at all times requiring long-term use of these semi-opaque contact lenses while other may retrain to completely clear lens segments 63.

Recent evidence that attention plays an essential role to almost all other brain functions including motor functioning in stroke patients with hemiparesis or hemiplegia, suggest that any technique that can improve attention related to brain injury, might help in the recovery of many non-vision related brain functions. In addition, some research has established a relationship between hemispheric attention and visual processing in the dysfunction of developmental reading disorder, the most common type of learning disability. With reading and language processing skewed towards left hemisphere functioning, and spatial, arithmetic and social/emotional sensibilities skewed towards right hemisphere processing, the use of hemi-lenses to effectively block and isolate specific areas of brain functioning might be effective is generating useful information and greater understanding of the brain's functioning.

Examples Include:

Treatment of stroke-related motor programming problems. Recent evidence that attention plays an role essential to almost all other brain functions including motor functioning in stroke patients with hemiparesis or hemiplegia, suggest that any technique that can improve attention related to brain injury, might help in the recovery of many non-vision related brain functions. Hemi-lenses used as an adjunctive device in tandem with the tradition rehabilitation therapies including physical and occupational therapy have the potential to accelerate the restoration of muscle tone and control, balance, and coordination, in addition to the possibility that recovery of hemispheric specific attention could reduce or relieve hemiplegia, hemiparesis, and/or contactures associated with nonuse.

Treatment of Developmental Reading Disorder

Some research has established a relationship between hemispheric attention and visual processing in the dysfunction of developmental reading disorder, the most common type of learning disability. With reading and language processing skewed towards left hemisphere functioning, selective blockage of the left visual field may produce more effective processing of visual symbol decoding in reading.

Use as a diagnostic tool in the neurology setting

Patients with intractable epilepsy often undergo a specialized invasive procedure known as the Wada procedure. In this procedure, Sodium amytol is injected in the internal carotid artery of the patient, effectively putting one hemisphere "to sleep" for several minutes, while the other hemisphere remains functionally normal. The neurologist and neuropsychologist can then perform a series of cognitive tests to evaluate the integrity of functioning of the intact hemisphere in an effort to isolate the focus of the seizure disorder. This technique is often unpredictable, and because the anesthesia is short-lived the quantity of data available for collection is limited. With hemi-lenses, the neurologist and neuropsychologist can evaluate similar isolation of hemispheric performance without the time constraints and confounds produced by drug induced mental status changes.

Hemi-lenses could also be used in the diagnosis of epilepsy as a useful addition to the standard electroencephalogram (EEG) procedure. This noninvasive neurodiagnostic procedure utilizing external electrodes placed about the skull architecture to sense and record brain electrical activity typically requires that the patient submit to photic stimulation with rhythmic strobe light exposure. Hemi-lenses could be used to further isolate brain electrical activity in each hemisphere by selectively blocking visual input. In the evoked potential variant of the EEG, where brain activity is recorded in response to specific stimulation, the use of hemi-lenses again could further articulate the functioning of an exposed hemisphere, as well as brain activity across the corpus callosum and into the hemisphere that has sensory block.

Use in functional assessment of cognitive skills

Neuropsychologists can use hemi-lenses to functionally assess hemispheric functioning by selectively presenting information that either coincides or interferes with the unblocked visual field. These procedures can help clarify the role of each hemisphere in acquisition of information and interference with acquisition.

Performance enhancement training

Hemi-lenses could also be effective in visual training in non-medical settings. For example, baseball batters use asymmetric visual information when standing at the plate judging pitches. The use of hemi-lenses to isolate the field that captures the pitcher and pitch, and block the catcher, umpire, and other distractions might significantly improve batting performance. Golfers might also benefit from the use of hemi-lenses to limit interference from visual distractions that occur behind the vector line beginning with the ball tee. Tennis players might utilize hemi-lenses to aid in visual tracking and concentration during backhand practice.

Use as a research tool

In addition to left hemispheric specialization related to reading and language, spatial, arithmetic and social/emotional sensibilities are skewed towards right hemisphere processing. The use of hemi-lenses to effectively block and isolate specific areas of brain functioning might be effective as generating useful information and greater understanding of the brain's functioning.

The present invention has been described with reference to certain preferred and alternative embodiments that are intended to be exemplary only and not limiting to the full scope of the present invention as set forth in the appended claims.

What is claimed is:

1. A contacts lens kit for use in training or rehabilitating targeted areas of a brain of a person, the kit comprising:
    a plurality of contact lenses having occluded areas covering a portion of the pupil area of the contact lens,
    the plurality of contact lenses including a first contact lens for use on the right eye or the left eye of the person, wherein the occluded area of the first contact lens has a degree of opacity between 100% and 10%,
    the plurality of contact lenses further comprising a second contact lens for use on the same one of the right eye or left eye as the first contact lens, wherein the occluded area of the second contact lens has a degree of opacity less than the degree of opacity of the occluded area of the first contact lens.

2. The contact lens kit of claim 1 wherein the occluded areas comprise radial segments of the contact lenses.

3. The contact lens kit of claim 1 wherein the occluded area covers approximately one of a one quadrant, two quadrant, or three quadrant sector of the pupil area.

4. The contact lens kit of claim 1 wherein the occluded area covers approximately the left half or right half of the pupil area.

5. The contact lens kit of claim 1 wherein the contact lens further comprises means for preventing rotation of the contact lens on the eye of the person.

6. The contact lens kit of claim 5 wherein the occluded area has a border with a non-occluded area in the pupil area of the lens, and the border being positioned on the contact lens such that the border is substantially vertical when the lens is worn on the eye of the patient.

7. A method of training and rehabilitation of a targeted area of the brain of a person, comprising the steps of:

(a) placing a contact lens on each eye of the person, each of said contact lens having an occluded area comprising a radial segment of substantially greater than 180° of said contacts lens, said occluded area selected so as to force visual processing to the targeted area of the brain and said occluded area having a degree of opacity allowing some visual processing to be conducted in non-targeted areas of the brain; and (b) having the person perform everyday visual and non-visual tasks selected to stimulate the targeted area of the brain.

8. The method of claim 7 wherein said degree of opacity of said occluded area is between 90% and 10%.

9. The method of claim 7 wherein said contact lens further comprises means for preventing rotation of said contact lens on the eye of the person.

10. A method of training and rehabilitation of a targeted area of the brain of a person, comprising the steps of:

(a) placing a contact lens on each eye of the person, each of said contact lens having an occluded area comprising a radial segment of substantially less than 180° of said contacts lens, said occluded area selected so as to force visual processing to the targeted area of the brain and said occluded area having a degree of opacity allowing some visual processing to be conducted in non-targeted areas of the brain; and (b) having the person perform everyday visual and non-visual tasks selected to stimulate the targeted area of the brain.

11. The method of claim 10 wherein said degree of opacity of said occluded area is between 90% and 10%.

12. The method of claim 10 wherein said contact lens further comprises means for preventing rotation of said contact lens on the eye of the person.

13. A device for training and rehabilitation of a targeted area of the brain of a person, comprising:

a contact lens having an occluded area comprising a radial segment of substantially greater than 180° of said contact lens, said occluded area selected so as to force visual processing to the targeted area of the brain and said occluded area having a degree of opacity allowing some visual processing to be conducted in non-targeted areas of the brain while the person performs everyday visual and non-visual tasks to stimulate the targeted area of the brain.

14. The device of claim 13 wherein said degree of opacity of said occluded area is around 100%.

15. The device of claim 13 wherein said contact lens further comprises means for preventing rotation of said contact lens on the eye of the person.

16. A device for training and rehabilitation of a targeted area of the brain of a person, comprising:

a contact lens having an occluded area comprising a radial segment of substantially less than 180° of said contact lens, said occluded area selected so as to force visual processing to the targeted area of the brain and said occluded area having a degree of opacity allowing some visual processing to be conducted in non-targeted areas of the brain while the person performs everyday visual and non-visual tasks to stimulate the targeted area of the brain.

17. The device of claim 16 wherein said degree of opacity of said occluded area is around 100%.

18. The device of claim 16 wherein said contact lens further comprises means for preventing rotation of said contact lens on the eye of the person.

* * * * *